United States Patent
Johnson et al.

(10) Patent No.: US 7,951,150 B2
(45) Date of Patent: May 31, 2011

(54) VESSEL SEALER AND DIVIDER WITH ROTATING SEALER AND CUTTER

(75) Inventors: Kristin D. Johnson, Louisville, CO (US); Steven P. Buysse, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 12/710,033

(22) Filed: Feb. 22, 2010

(65) Prior Publication Data
US 2010/0145335 A1  Jun. 10, 2010

Related U.S. Application Data

(62) Division of application No. 11/328,767, filed on Jan. 10, 2006, now Pat. No. 7,686,804.

(60) Provisional application No. 60/644,487, filed on Jan. 14, 2005.

(51) Int. Cl.
*A61B 18/14* (2006.01)
(52) U.S. Cl. ............................................. 606/51; 606/52
(58) Field of Classification Search ................ 606/51–52
See application file for complete search history.

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |

(Continued)

FOREIGN PATENT DOCUMENTS

CA  2104423  2/1994

(Continued)

OTHER PUBLICATIONS

U.S. Appl. No. 12/248,104, filed Oct. 9, 2008.

(Continued)

*Primary Examiner* — Michael Peffley
*Assistant Examiner* — Samantha Good

(57) ABSTRACT

An electrosurgical instrument includes a housing having a shaft attached thereto which defines a longitudinal axis therethrough. The instrument also includes first and second opposing jaw members coupled to the shaft, the first jaw member having a conductive surface and movable relative to the second jaw member. The second jaw member is fixed relative to the shaft and includes an electrode rotatable along the longitudinal axis. The rotatable electrode has a sealing surface and a cutting edge. One or more non-conductive stop members are disposed on the first and/or second jaw members that are dimensioned to control the distance between the electrically conductive surfaces when tissue is held therebetween. The jaw members are connected to an electrosurgical energy source such that the jaw members are capable of conducting energy through tissue held therebetween.

9 Claims, 5 Drawing Sheets

U.S. PATENT DOCUMENTS

| | | |
|---|---|---|
| 2,668,538 A | 2/1954 | Baker |
| 2,796,065 A | 6/1957 | Kapp |
| 3,073,311 A | 1/1963 | Tibbs et al. |
| 3,100,489 A | 8/1963 | Bagley |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,805,616 A | 2/1989 | Pao |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |

| | | | | | |
|---|---|---|---|---|---|
| 5,374,277 A | 12/1994 | Hassler | 5,564,615 A | 10/1996 | Bishop et al. |
| 5,376,089 A | 12/1994 | Smith | 5,569,241 A | 10/1996 | Edwards |
| 5,376,094 A | 12/1994 | Kline | 5,569,243 A | 10/1996 | Kortenbach et al. |
| D354,564 S | 1/1995 | Medema | 5,571,100 A | 11/1996 | Goble et al. |
| 5,383,875 A | 1/1995 | Bays et al. | 5,573,424 A | 11/1996 | Poppe |
| 5,383,880 A | 1/1995 | Hooven | 5,573,534 A | 11/1996 | Stone |
| 5,383,897 A | 1/1995 | Wholey | 5,573,535 A | 11/1996 | Viklund |
| 5,389,098 A | 2/1995 | Tsuruta et al. | 5,575,799 A | 11/1996 | Bolanos et al. |
| 5,389,103 A | 2/1995 | Melzer et al. | 5,575,805 A | 11/1996 | Li |
| 5,389,104 A | 2/1995 | Hahnen et al. | 5,578,052 A | 11/1996 | Koros et al. |
| 5,391,166 A | 2/1995 | Eggers | 5,579,781 A | 12/1996 | Cooke |
| 5,391,183 A | 2/1995 | Janzen et al. | 5,582,611 A | 12/1996 | Tsuruta et al. |
| 5,395,360 A | 3/1995 | Manoukian | 5,582,617 A | 12/1996 | Klieman et al. |
| 5,396,900 A | 3/1995 | Slater et al. | 5,585,896 A | 12/1996 | Yamazaki et al. |
| 5,403,312 A | 4/1995 | Yates et al. | 5,590,570 A | 1/1997 | LeMaire, III et al. |
| 5,403,342 A | 4/1995 | Tovey et al. | 5,591,181 A | 1/1997 | Stone et al. |
| 5,405,344 A | 4/1995 | Williamson et al. | 5,597,107 A | 1/1997 | Knodel et al. |
| 5,409,763 A | 4/1995 | Serizawa et al. | 5,599,350 A | 2/1997 | Schulze et al. |
| 5,411,519 A | 5/1995 | Tovey et al. | 5,601,224 A | 2/1997 | Bishop et al. |
| 5,411,520 A | 5/1995 | Nash et al. | 5,601,601 A | 2/1997 | Tal et al. |
| 5,413,571 A | 5/1995 | Katsaros et al. | 5,601,641 A | 2/1997 | Stephens |
| 5,415,656 A | 5/1995 | Tihon et al. | 5,603,711 A | 2/1997 | Parins et al. |
| 5,415,657 A | 5/1995 | Taymor-Luria | 5,603,723 A | 2/1997 | Aranyi et al. |
| 5,417,709 A | 5/1995 | Slater | 5,607,436 A | 3/1997 | Pratt et al. |
| 5,422,567 A | 6/1995 | Matsunaga | 5,611,798 A | 3/1997 | Eggers |
| 5,423,810 A | 6/1995 | Goble et al. | 5,611,808 A | 3/1997 | Hossain et al. |
| 5,425,690 A | 6/1995 | Chang | 5,611,813 A | 3/1997 | Lichtman |
| 5,425,739 A | 6/1995 | Jessen | 5,620,415 A | 4/1997 | Lucey et al. |
| 5,429,616 A | 7/1995 | Schaffer | 5,620,453 A | 4/1997 | Nallakrishnan |
| 5,431,672 A | 7/1995 | Cote et al. | 5,620,459 A | 4/1997 | Lichtman |
| 5,431,674 A | 7/1995 | Basile et al. | 5,624,452 A | 4/1997 | Yates |
| 5,437,292 A | 8/1995 | Kipshidze et al. | 5,626,578 A | 5/1997 | Tihon |
| 5,438,302 A | 8/1995 | Goble | 5,626,609 A | 5/1997 | Zvenyatsky et al. |
| 5,439,478 A | 8/1995 | Palmer | 5,630,833 A | 5/1997 | Katsaros et al. |
| 5,441,517 A | 8/1995 | Kensey et al. | 5,637,110 A | 6/1997 | Pennybacker et al. |
| 5,443,463 A | 8/1995 | Stern et al. | 5,638,003 A | 6/1997 | Hall |
| 5,443,464 A | 8/1995 | Russell et al. | 5,643,294 A | 7/1997 | Tovey et al. |
| 5,443,480 A | 8/1995 | Jacobs et al. | 5,647,869 A | 7/1997 | Goble et al. |
| 5,445,638 A | 8/1995 | Rydell et al. | 5,647,871 A | 7/1997 | Levine et al. |
| 5,445,658 A | 8/1995 | Durrfeld et al. | 5,649,959 A | 7/1997 | Hannam et al. |
| 5,449,480 A | 9/1995 | Kuriya et al. | 5,655,650 A | 8/1997 | Naitou |
| 5,451,224 A | 9/1995 | Goble et al. | 5,658,281 A | 8/1997 | Heard |
| 5,454,809 A | 10/1995 | Janssen | D384,413 S | 9/1997 | Zlock et al. |
| 5,454,823 A | 10/1995 | Richardson et al. | 5,662,667 A | 9/1997 | Knodel |
| 5,454,827 A | 10/1995 | Aust et al. | 5,665,100 A | 9/1997 | Yoon |
| 5,456,684 A | 10/1995 | Schmidt et al. | 5,667,526 A | 9/1997 | Levin |
| 5,458,598 A | 10/1995 | Feinberg et al. | 5,674,220 A | 10/1997 | Fox et al. |
| 5,460,629 A | 10/1995 | Shlain et al. | 5,674,229 A | 10/1997 | Tovey et al. |
| 5,461,765 A | 10/1995 | Linden et al. | 5,681,282 A | 10/1997 | Eggers et al. |
| 5,462,546 A | 10/1995 | Rydell | 5,688,270 A | 11/1997 | Yates et al. |
| 5,472,442 A | 12/1995 | Klicek | 5,690,652 A | 11/1997 | Wurster et al. |
| 5,472,443 A | 12/1995 | Cordis et al. | 5,690,653 A | 11/1997 | Richardson et al. |
| 5,478,351 A | 12/1995 | Meade et al. | 5,693,051 A | 12/1997 | Schulze et al. |
| 5,480,406 A | 1/1996 | Nolan et al. | 5,693,920 A | 12/1997 | Maeda |
| 5,480,409 A | 1/1996 | Riza | 5,695,522 A | 12/1997 | LeMaire, III et al. |
| 5,484,436 A | 1/1996 | Eggers et al. | 5,700,261 A | 12/1997 | Brinkerhoff |
| 5,496,312 A | 3/1996 | Klicek | 5,700,270 A | 12/1997 | Peyser et al. |
| 5,496,317 A | 3/1996 | Goble et al. | 5,702,390 A | 12/1997 | Austin et al. |
| 5,496,347 A | 3/1996 | Hashiguchi et al. | 5,707,369 A | 1/1998 | Vaitekunas et al. |
| 5,499,997 A | 3/1996 | Sharpe et al. | 5,709,680 A | 1/1998 | Yates et al. |
| 5,509,922 A | 4/1996 | Aranyi et al. | 5,716,366 A | 2/1998 | Yates |
| 5,512,721 A | 4/1996 | Young et al. | 5,720,744 A | 2/1998 | Eggleston et al. |
| 5,514,134 A | 5/1996 | Rydell et al. | 5,722,421 A | 3/1998 | Francese et al. |
| 5,520,702 A | 5/1996 | Sauer et al. | 5,725,536 A | 3/1998 | Oberlin et al. |
| 5,527,313 A | 6/1996 | Scott et al. | 5,727,428 A | 3/1998 | LeMaire, III et al. |
| 5,528,833 A | 6/1996 | Sakuma | 5,735,848 A | 4/1998 | Yates et al. |
| 5,529,067 A | 6/1996 | Larsen et al. | 5,743,906 A | 4/1998 | Parins et al. |
| 5,531,744 A | 7/1996 | Nardella et al. | 5,752,973 A | 5/1998 | Kieturakis |
| 5,536,251 A | 7/1996 | Evard et al. | 5,755,717 A | 5/1998 | Yates et al. |
| 5,540,684 A | 7/1996 | Hassler, Jr. | 5,759,188 A | 6/1998 | Yoon |
| 5,540,685 A | 7/1996 | Parins et al. | 5,762,255 A | 6/1998 | Chrisman et al. |
| 5,540,706 A | 7/1996 | Aust et al. | 5,762,609 A | 6/1998 | Benaron et al. |
| 5,540,715 A | 7/1996 | Katsaros et al. | 5,766,130 A | 6/1998 | Selmonosky |
| 5,542,945 A | 8/1996 | Fritzsch | 5,766,166 A | 6/1998 | Hooven |
| 5,558,671 A | 9/1996 | Yates | 5,766,170 A | 6/1998 | Eggers |
| 5,558,672 A | 9/1996 | Edwards et al. | 5,766,196 A | 6/1998 | Griffiths |
| 5,562,619 A | 10/1996 | Mirarchi et al. | 5,769,849 A | 6/1998 | Eggers |
| 5,562,699 A | 10/1996 | Heimberger et al. | 5,772,655 A | 6/1998 | Bauer et al. |
| 5,562,720 A | 10/1996 | Stern et al. | 5,772,670 A | 6/1998 | Brosa |

| Patent | Date | Inventor |
|---|---|---|
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| 5,779,727 A | 7/1998 | Orejola |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Dafforn et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |

| | | |
|---|---|---|
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| D465,281 S | 11/2002 | Lang |
| D466,209 S | 11/2002 | Bon |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,285 B2 | 11/2004 | Laufer et al. |
| 6,835,200 B2 | 12/2004 | Laufer et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |

| Patent | Type | Date | Inventors |
|---|---|---|---|
| 6,994,707 | B2 | 2/2006 | Ellman et al. |
| 6,994,709 | B2 | 2/2006 | Iida |
| 6,997,931 | B2 | 2/2006 | Sauer et al. |
| 7,001,381 | B2 | 2/2006 | Harano et al. |
| 7,011,657 | B2 | 3/2006 | Truckai et al. |
| 7,033,354 | B2 | 4/2006 | Keppel |
| 7,033,356 | B2 | 4/2006 | Latterell et al. |
| 7,041,102 | B2 | 5/2006 | Truckai et al. |
| 7,044,948 | B2 | 5/2006 | Keppel |
| 7,052,489 | B2 | 5/2006 | Griego et al. |
| 7,052,496 | B2 | 5/2006 | Yamauchi |
| 7,063,715 | B2 | 6/2006 | Onuki et al. |
| D525,361 | S | 7/2006 | Hushka |
| 7,070,597 | B2 | 7/2006 | Truckai et al. |
| 7,083,618 | B2 | 8/2006 | Couture et al. |
| 7,083,619 | B2 | 8/2006 | Truckai et al. |
| 7,083,620 | B2 | 8/2006 | Jahns et al. |
| 7,087,051 | B2 | 8/2006 | Bourne et al. |
| 7,087,054 | B2 | 8/2006 | Truckai et al. |
| 7,090,673 | B2 | 8/2006 | Dycus et al. |
| 7,090,689 | B2 | 8/2006 | Nagase et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,103,947 | B2 | 9/2006 | Sartor et al. |
| 7,107,124 | B2 | 9/2006 | Green |
| 7,112,199 | B2 | 9/2006 | Cosmescu |
| D531,311 | S | 10/2006 | Guerra et al. |
| 7,115,123 | B2 | 10/2006 | Knowlton et al. |
| 7,118,570 | B2 | 10/2006 | Tetzlaff et al. |
| 7,118,587 | B2 | 10/2006 | Dycus et al. |
| 7,131,860 | B2 | 11/2006 | Sartor et al. |
| 7,131,970 | B2 | 11/2006 | Moses et al. |
| 7,131,971 | B2 | 11/2006 | Dycus et al. |
| 7,135,020 | B2 | 11/2006 | Lawes et al. |
| 7,137,980 | B2 | 11/2006 | Buysse et al. |
| D533,942 | S | 12/2006 | Kerr et al. |
| 7,145,757 | B2 | 12/2006 | Shea et al. |
| 7,147,638 | B2 | 12/2006 | Chapman et al. |
| 7,150,097 | B2 | 12/2006 | Sremcich et al. |
| 7,150,749 | B2 | 12/2006 | Dycus et al. |
| 7,153,314 | B2 | 12/2006 | Laufer et al. |
| D535,027 | S | 1/2007 | James et al. |
| 7,156,842 | B2 | 1/2007 | Sartor et al. |
| 7,156,846 | B2 | 1/2007 | Dycus et al. |
| 7,160,298 | B2 | 1/2007 | Lawes et al. |
| 7,160,299 | B2 | 1/2007 | Baily |
| 7,166,106 | B2 | 1/2007 | Bartel et al. |
| 7,169,145 | B2 | 1/2007 | Isaacson et al. |
| 7,169,146 | B2 | 1/2007 | Truckai et al. |
| 7,179,255 | B2 | 2/2007 | Lettice et al. |
| 7,179,258 | B2 | 2/2007 | Buysse et al. |
| 7,195,631 | B2 | 3/2007 | Dumbauld |
| D541,418 | S | 4/2007 | Schechter et al. |
| 7,207,990 | B2 | 4/2007 | Lands et al. |
| D541,938 | S | 5/2007 | Kerr et al |
| 7,223,264 | B2 | 5/2007 | Daniel et al. |
| 7,223,265 | B2 | 5/2007 | Keppel |
| D545,432 | S | 6/2007 | Watanabe |
| 7,232,440 | B2 | 6/2007 | Dumbauld et al. |
| 7,238,184 | B2 | 7/2007 | Megerman et al. |
| 7,241,288 | B2 | 7/2007 | Braun |
| 7,241,296 | B2 | 7/2007 | Buysse et al. |
| 7,244,257 | B2 | 7/2007 | Podjahsky et al. |
| 7,246,734 | B2 | 7/2007 | Shelto, IV |
| 7,248,944 | B2 | 7/2007 | Green |
| 7,252,667 | B2 | 8/2007 | Moses et al. |
| 7,255,697 | B2 | 8/2007 | Dycus et al. |
| 7,267,677 | B2 | 9/2007 | Johnson et al. |
| 7,270,660 | B2 | 9/2007 | Ryan |
| 7,270,664 | B2 | 9/2007 | Johnson et al. |
| 7,276,068 | B2 | 10/2007 | Johnson et al. |
| 7,300,435 | B2 | 11/2007 | Wham et al. |
| 7,303,557 | B2 | 12/2007 | Wham et al. |
| 7,311,709 | B2 | 12/2007 | Truckai et al. |
| 7,314,471 | B2 | 1/2008 | Holman |
| 7,318,823 | B2 | 1/2008 | Sharps et al. |
| 7,329,256 | B2 | 2/2008 | Johnson et al. |
| 7,329,257 | B2 | 2/2008 | Kanehira et al. |
| D564,662 | S | 3/2008 | Moses et al. |
| 7,338,526 | B2 | 3/2008 | Steinberg |
| 7,342,754 | B2 | 3/2008 | Fitzgerald et al. |
| 7,344,268 | B2 | 3/2008 | Jhigamian |
| D567,943 | S | 4/2008 | Moses et al. |
| 7,354,440 | B2 | 4/2008 | Truckal et al. |
| 7,367,976 | B2 | 5/2008 | Lawes et al. |
| 7,377,920 | B2 | 5/2008 | Buysse et al. |
| 7,384,420 | B2 | 6/2008 | Dycus et al. |
| 7,384,421 | B2 | 6/2008 | Hushka |
| 7,396,336 | B2 | 7/2008 | Orszulak et al. |
| D575,395 | S | 8/2008 | Hushka |
| D575,401 | S | 8/2008 | Hixson et al. |
| 7,425,835 | B2 | 9/2008 | Eisele |
| 7,431,721 | B2 | 10/2008 | Paton et al. |
| 7,435,249 | B2 | 10/2008 | Buysse et al. |
| 7,442,193 | B2 | 10/2008 | Shields et al. |
| 7,442,194 | B2 | 10/2008 | Dumbauld et al. |
| 7,445,621 | B2 | 11/2008 | Dumbauld et al. |
| 7,458,972 | B2 | 12/2008 | Keppel |
| 7,473,253 | B2 | 1/2009 | Dycus et al. |
| 7,481,810 | B2 | 1/2009 | Dumbauld et al. |
| 7,487,780 | B2 | 2/2009 | Hooven |
| 7,491,201 | B2 | 2/2009 | Shields et al. |
| 7,491,202 | B2 | 2/2009 | Odom et al. |
| 7,500,975 | B2 | 3/2009 | Cunningham et al. |
| 7,503,474 | B2 | 3/2009 | Hillstead et al. |
| 7,510,556 | B2 | 3/2009 | Nguyen et al. |
| 7,513,898 | B2 | 4/2009 | Johnson et al. |
| 7,517,351 | B2 | 4/2009 | Culp et al. |
| 7,540,872 | B2 | 6/2009 | Schechter et al. |
| 7,549,995 | B2 | 6/2009 | Schultz |
| 7,553,312 | B2 | 6/2009 | Tetzlaff et al. |
| 7,582,087 | B2 | 9/2009 | Tetzlaff et al. |
| 7,588,565 | B2 | 9/2009 | Marchitto et al. |
| 7,594,916 | B2 | 9/2009 | Weinberg |
| 7,597,693 | B2 | 10/2009 | Garrison |
| 7,621,910 | B2 | 11/2009 | Sugi |
| 7,628,791 | B2 | 12/2009 | Garrison et al. |
| 7,628,792 | B2 | 12/2009 | Guerra |
| 7,641,653 | B2 | 1/2010 | Dalla Betta et al. |
| 7,651,493 | B2 | 1/2010 | Arts et al. |
| 7,651,494 | B2 | 1/2010 | McClurken et al. |
| 7,655,007 | B2 | 2/2010 | Baily |
| 7,678,111 | B2 | 3/2010 | Mulier et al. |
| 7,686,804 | B2 | 3/2010 | Johnson et al. |
| 7,686,827 | B2 | 3/2010 | Hushka |
| 2002/0107517 | A1 | 8/2002 | Witt et al. |
| 2002/0111624 | A1 | 8/2002 | Witt et al. |
| 2002/0188294 | A1* | 12/2002 | Couture et al. ............ 606/51 |
| 2003/0014052 | A1 | 1/2003 | Buysse et al. |
| 2003/0014053 | A1 | 1/2003 | Nguyen et al. |
| 2003/0018332 | A1 | 1/2003 | Schmaltz et al. |
| 2003/0069570 | A1 | 4/2003 | Witzel et al. |
| 2003/0109875 | A1 | 6/2003 | Tetzlaff et al. |
| 2003/0114851 | A1 | 6/2003 | Truckai et al. |
| 2003/0139741 | A1 | 7/2003 | Goble et al. |
| 2003/0158548 | A1 | 8/2003 | Phan et al. |
| 2003/0158549 | A1 | 8/2003 | Swanson |
| 2003/0171747 | A1 | 9/2003 | Kanehira et al. |
| 2003/0181910 | A1 | 9/2003 | Dycus et al. |
| 2003/0216732 | A1 | 11/2003 | Truckai et al. |
| 2003/0229344 | A1 | 12/2003 | Dycus et al. |
| 2003/0236325 | A1 | 12/2003 | Bonora |
| 2004/0030330 | A1 | 2/2004 | Brassell et al. |
| 2004/0064151 | A1 | 4/2004 | Mollenauer |
| 2004/0073238 | A1 | 4/2004 | Makower |
| 2004/0073256 | A1 | 4/2004 | Marchitto et al. |
| 2004/0115296 | A1 | 6/2004 | Duffin |
| 2004/0143263 | A1 | 7/2004 | Schechter et al. |
| 2004/0148035 | A1 | 7/2004 | Barrett et al. |
| 2004/0199181 | A1 | 10/2004 | Knodel et al. |
| 2004/0210282 | A1 | 10/2004 | Flock et al. |
| 2004/0224590 | A1 | 11/2004 | Rawa et al. |
| 2004/0236326 | A1 | 11/2004 | Schulze et al. |
| 2004/0249374 | A1 | 12/2004 | Tetzlaff et al. |
| 2004/0260281 | A1 | 12/2004 | Baxter, III et al. |
| 2005/0004564 | A1 | 1/2005 | Wham et al. |
| 2005/0004569 | A1 | 1/2005 | Witt et al. |

| | | |
|---|---|---|
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0096645 A1 | 5/2005 | Wellman et al. |
| 2005/0101952 A1 | 5/2005 | Lands et al. |
| 2005/0149017 A1 | 7/2005 | Dycus |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0052778 A1 | 3/2006 | Chapman et al. |
| 2006/0052779 A1 | 3/2006 | Hammill |
| 2006/0064086 A1 | 3/2006 | Odom |
| 2006/0079888 A1 | 4/2006 | Mulier et al. |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0116675 A1 | 6/2006 | McClurken et al. |
| 2006/0129146 A1 | 6/2006 | Dycus et al. |
| 2006/0167452 A1 | 7/2006 | Moses et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0173804 A1 | 7/2007 | Wham et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0198011 A1 | 8/2007 | Sugita |
| 2007/0208339 A1 | 9/2007 | Arts et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0125767 A1 | 5/2008 | Blaha |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248021 A1 | 10/2009 | Mckenna |
| 2009/0261804 A1 | 10/2009 | Mckenna et al. |
| 2009/0306660 A1 | 12/2009 | Johnson et al. |
| 2010/0016857 A1 | 1/2010 | Mckenna et al. |
| 2010/0023009 A1 | 1/2010 | Moses et al. |
| 2010/0036375 A1 | 2/2010 | Regadas |
| 2010/0042100 A1 | 2/2010 | Tetzlaff et al. |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3423356 | 1/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |

| | | | | | | |
|---|---|---|---|---|---|---|
| DE | 10045375 | 4/2002 | | JP | 08252263 | 10/1996 |
| DE | 20 2007 009317 | 10/2007 | | JP | 09010223 | 1/1997 |
| DE | 19738457 | 1/2009 | | JP | 11-070124 | 5/1998 |
| EP | 0364216 | 4/1990 | | JP | 2000-102545 | 9/1998 |
| EP | 0467501 | 1/1992 | | JP | 11244298 | 9/1999 |
| EP | 0509670 | 10/1992 | | JP | 2000-342599 | 12/2000 |
| EP | 0518230 | 12/1992 | | JP | 2000-350732 | 12/2000 |
| EP | 0541930 | 5/1993 | | JP | 2001-008944 | 1/2001 |
| EP | 0572131 | 12/1993 | | JP | 2001-029356 | 2/2001 |
| EP | 0584787 | 3/1994 | | JP | 2001-128990 | 5/2001 |
| EP | 0589453 | 3/1994 | | SU | 401367 | 11/1974 |
| EP | 0589555 | 3/1994 | | WO | WO 89/00757 | 1/1989 |
| EP | 0623316 | 11/1994 | | WO | WO 92/04873 | 4/1992 |
| EP | 0624348 | 11/1994 | | WO | WO 92/06642 | 4/1992 |
| EP | 0650701 | 5/1995 | | WO | WO 93/19681 | 10/1993 |
| EP | 0694290 | 3/1996 | | WO | WO 93/21845 | 11/1993 |
| EP | 0717966 | 6/1996 | | WO | WO 94/08524 | 4/1994 |
| EP | 0754437 | 3/1997 | | WO | WO 94/20025 | 9/1994 |
| EP | 0517243 | 9/1997 | | WO | WO 95/02369 | 1/1995 |
| EP | 0853922 | 7/1998 | | WO | WO 95/07662 | 3/1995 |
| EP | 0875209 | 11/1998 | | WO | WO 95/15124 | 6/1995 |
| EP | 0878169 | 11/1998 | | WO | WO 95/20360 | 8/1995 |
| EP | 0887046 | 1/1999 | | WO | WO 96/05776 | 2/1996 |
| EP | 0923907 | 6/1999 | | WO | WO 96/11635 | 4/1996 |
| EP | 0950378 | 10/1999 | | WO | WO 96/22056 | 7/1996 |
| EP | 0986990 | 3/2000 | | WO | WO 96/13218 | 9/1996 |
| EP | 1034747 | 9/2000 | | WO | WO 97/00646 | 1/1997 |
| EP | 1034748 | 9/2000 | | WO | WO 97/00647 | 1/1997 |
| EP | 1025807 | 10/2000 | | WO | WO 97/10764 | 3/1997 |
| EP | 1034746 | 10/2000 | | WO | WO 97/18768 | 5/1997 |
| EP | 1050278 | 11/2000 | | WO | WO 97/24073 | 7/1997 |
| EP | 1053719 | 11/2000 | | WO | WO 97/24993 | 7/1997 |
| EP | 1053720 | 11/2000 | | WO | WO 98/14124 | 4/1998 |
| EP | 1055399 | 11/2000 | | WO | WO 98/27880 | 7/1998 |
| EP | 1055400 | 11/2000 | | WO | WO 98/43264 | 10/1998 |
| EP | 1080694 | 3/2001 | | WO | WO 99/03407 | 1/1999 |
| EP | 1082944 | 3/2001 | | WO | WO 99/03408 | 1/1999 |
| EP | 1159926 | 12/2001 | | WO | WO 99/03409 | 1/1999 |
| EP | 1177771 | 2/2002 | | WO | WO 99/03414 | 1/1999 |
| EP | 1278007 | 1/2003 | | WO | WO 99/12488 | 3/1999 |
| EP | 1301135 | 4/2003 | | WO | WO 99/23933 | 5/1999 |
| EP | 1330991 | 7/2003 | | WO | WO 99/40857 | 8/1999 |
| EP | 1486177 | 6/2004 | | WO | WO 99/40861 | 8/1999 |
| EP | 1472984 | 11/2004 | | WO | WO 99/51158 | 10/1999 |
| EP | 0774232 | 1/2005 | | WO | WO 99/66850 | 12/1999 |
| EP | 1527747 | 5/2005 | | WO | WO 00/24330 | 5/2000 |
| EP | 1530952 | 5/2005 | | WO | WO 00/24331 | 5/2000 |
| EP | 1532932 | 5/2005 | | WO | WO 00/36986 | 6/2000 |
| EP | 1535581 | 6/2005 | | WO | WO 00/41638 | 7/2000 |
| EP | 1609430 | 12/2005 | | WO | WO 00/47124 | 8/2000 |
| EP | 1632192 | 3/2006 | | WO | WO 00/53112 | 9/2000 |
| EP | 1642543 | 4/2006 | | WO | WO 01/01847 | 1/2001 |
| EP | 1645238 | 4/2006 | | WO | WO 01/17448 | 3/2001 |
| EP | 1645240 | 4/2006 | | WO | WO 01/54604 | 8/2001 |
| EP | 1649821 | 4/2006 | | WO | WO 02/07627 | 1/2002 |
| EP | 1707143 | 10/2006 | | WO | WO 02/067798 | 9/2002 |
| EP | 1767163 | 3/2007 | | WO | WO 02/080783 | 10/2002 |
| EP | 1769765 | 4/2007 | | WO | WO 02/080784 | 10/2002 |
| EP | 1769766 | 4/2007 | | WO | WO 02/080785 | 10/2002 |
| EP | 1785101 | 5/2007 | | WO | WO 02/080786 | 10/2002 |
| EP | 1810625 | 7/2007 | | WO | WO 02/080793 | 10/2002 |
| EP | 1810628 | 7/2007 | | WO | WO 02/080794 | 10/2002 |
| EP | 1842500 | 10/2007 | | SU | WO 02/080795 | 10/2002 |
| EP | 1878400 | 1/2008 | | WO | WO 02/080796 | 10/2002 |
| EP | 1929970 | 6/2008 | | WO | WO 02/080797 | 10/2002 |
| EP | 1990019 | 11/2008 | | WO | WO 02/080798 | 10/2002 |
| EP | 1683496 | 12/2008 | | WO | WO 02/080799 | 10/2002 |
| EP | 1527744 | 2/2009 | | WO | WO 02/081170 | 10/2002 |
| GB | 623316 | 5/1949 | | WO | WO 03/061500 | 7/2003 |
| GB | 1490585 | 11/1977 | | WO | WO 03/090630 | 11/2003 |
| GB | 2214430 A | 6/1989 | | WO | WO 03/101311 | 12/2003 |
| GB | 2213416 A | 8/1989 | | WO | WO 2004/028585 | 4/2004 |
| JP | 61-501068 | 9/1984 | | WO | WO 2004/032776 | 4/2004 |
| JP | 6-502328 | 3/1992 | | WO | WO 2004/032777 | 4/2004 |
| JP | 5-5106 | 1/1993 | | WO | WO 2004/052221 | 6/2004 |
| JP | 5-40112 | 2/1993 | | WO | WO 2004/073488 | 9/2004 |
| JP | 06343644 | 12/1994 | | WO | WO 2004/073490 | 9/2004 |
| JP | 07265328 | 10/1995 | | WO | WO 2004/073753 | 9/2004 |
| JP | 08056955 | 3/1996 | | WO | WO 2004/082495 | 9/2004 |

| | | |
|---|---|---|
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/048809 | 6/2005 |
| WO | WO 2005/050151 | 6/2005 |
| WO | WO 2005/110264 | 11/2005 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/039510 | 3/2009 |

OTHER PUBLICATIONS

U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548, 534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinckler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of the Gyrus PlasmaKinetic Sealer and the Valleylab LigaSure Device in the Hemostasis of Small, Medium, and Large-Sized Arteries"Carolinas Lapascopic and Advanced Surgery Program, Carolinas Medical Center, Charlotte, NC; date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Venous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007 .
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008 .
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009 .
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

US 7,951,150 B2

VESSEL SEALER AND DIVIDER WITH ROTATING SEALER AND CUTTER

CROSS REFERENCE TO RELATED APPLICATION

The present application is a divisional application of U.S. patent application Ser. No. 11/328,767, filed on Jan. 10, 2006 by Johnson et al., now U.S. Pat. No. 7,686,804, which claims the benefit of and priority to U.S. Provisional Application Ser. No. 60/644,487 filed on Jan. 14, 2005 by Johnson et al., the entire contents of each these applications being incorporated by reference herein.

BACKGROUND

The present disclosure relates to an electrosurgical instrument and method for performing endoscopic surgical procedures. More particularly, the present disclosure relates to an endoscopic bipolar electrosurgical forceps and method of using same which includes an end effector having a movable jaw and a fixed jaw, the fixed jaw including a rotatable electrode having a sealing surface and a cutting edge. Further, a non-conductive stop member is associated with one or both of the opposing jaw members. The non-conductive stop member is designed to control the gap distance between opposing jaw members and enhance the manipulation and gripping of tissue during the sealing and dividing process.

TECHNICAL FIELD

Endoscopic forceps utilize mechanical action to constrict, grasp, dissect and/or clamp tissue. Endoscopic electrosurgical forceps utilize both mechanical clamping action and electrical energy to effect hemostasis by heating the tissue and blood vessels to coagulate, cauterize and/or seal tissue.

Endoscopic instruments are inserted into the patient through a cannula, or port, that has been made with a trocar or similar such device. Typical sizes for cannulas range from three millimeters to twelve millimeters. Smaller cannulas are usually preferred, and this presents a design challenge to instrument manufacturers who must find ways to make surgical instruments that fit through the cannulas.

Certain endoscopic surgical procedures require cutting blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. However, if a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

As mentioned above, by utilizing an electrosurgical forceps, a surgeon can either cauterize, coagulate/desiccate and/or simply reduce or slow bleeding, by controlling the intensity, frequency and duration of the electrosurgical energy applied through jaw members to the tissue. The electrode of each jaw member is charged to a different electric potential such that when the jaw members grasp tissue, electrical energy can be selectively transferred through the tissue.

In order to effect a proper seal with larger vessels, two predominant mechanical parameters must be accurately controlled—the pressure applied to the vessel and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried. Vessel sealing is defined as the process of liquefying the collagen in the tissue so that it reforms into a fused mass. Thus, coagulation of small vessels is sufficient to permanently close them. Larger vessels need to be sealed to assure permanent closure.

U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the blood vessel and may result in an ineffective or non-uniform seal.

For the most part, these instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, the tissue may pre-maturely move prior to activation and sealing and/or a thicker, less reliable seal may be created.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Several attempts have been made to design an instrument which incorporates a knife or blade member which effectively severs the tissue after forming a tissue seal. For example, U.S. Pat. No. 5,674,220 to Fox et al. discloses a transparent vessel sealing instrument which includes a longitudinally reciprocating knife which severs the tissue once sealed. The instrument includes a plurality of openings which enable direct visualization of the tissue during the sealing and severing process. This direct visualization allows a user to visually and manually regulate the closure force and gap distance between jaw members to reduce and/or limit certain undesirable effects known to occur when sealing vessels, thermal spread, charring, etc. As can be appreciated, the overall success of creating a tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal.

U.S. Pat. Nos. 5,702,390 and 5,944,718 to Austin et al. disclose a vessel sealing instrument which includes a pivoting, triangularly-shaped electrode which is rotatable from a first position to coagulate tissue to a second position to cut tissue. As described above, the user must rely on direct visualization and expertise to control the various effects of sealing and cutting tissue. Additionally, since there is no means to control the gap distance, there is a risk of the electrodes of the instrument to come into contact with each other, regardless of the position of the triangularly-shaped electrode, and cause a short between electrodes resulting in damage to the instrument and/or connected energy source, e.g. electrosurgical generator. Further, to change operation of the instrument from coagulating to cutting, the instrument must be removed from the operative site and the electrode rotated by loosing a set screw which further adds time and complexity to the procedure.

Thus, a need exists to develop an endoscopic electrosurgical instrument which effectively and consistently seals and separates vascular tissue and solves the aforementioned problems. This instrument regulates the gap distances between opposing jaws members, reduces the chances of short circuiting the opposing jaws during activation and assists in manipulating, gripping and holding the tissue prior to and during activation and separation of the tissue.

SUMMARY

According to an aspect of the present disclosure, an electrosurgical instrument for sealing and dividing tissue includes a housing having a shaft attached thereto that defines a longitudinal axis. First and second opposing jaw members are coupled to the shaft; the first jaw member having a conductive surface and movable relative to the second jaw member and the second jaw member fixed relative to the shaft and having a conductive electrode rotatable along the longitudinal axis. The rotatable electrode includes a sealing surface on one side thereof and a cutting edge on a second side thereof. A source of electrosurgical energy is connected to each jaw member such that the jaw members are capable of conducting energy through tissue held therebetween. The electrosurgical instrument also includes one or more non-conductive stop members that are operatively associated with the first and/or second jaw members that are dimensioned to control the distance, e.g., gap, between the jaw members when tissue is held therebetween. The gap distance between the jaw members may be fixed and is typically in the range of about 0.001 inches to about 0.006 inches.

The electrosurgical instrument further includes a rotating assembly for rotating the electrode of the second jaw member and/or for rotating the second jaw member. The rotating assembly may include a dial disposed within the housing for setting a desired position of the electrode and an elongated tube disposed within the shaft coupling the dial to the electrode. The dial selectively orients the electrode of the second jaw member from a first operable position wherein the sealing surface of the electrode is generally parallel to the conductive surface of the first jaw member for sealing tissue to a second operable position wherein the cutting edge of the electrode is generally perpendicular to the conductive surface of the first jaw member for dividing tissue.

According to another aspect of the present disclosure, the forceps include a housing having a shaft attached thereto, the shaft defining a longitudinal axis. First and second opposing jaw members are coupled to the shaft; the first jaw member includes a conductive surface and is movable relative to the second jaw member and the second jaw member is fixed relative to the shaft and includes an electrode rotatable along the longitudinal axis. The rotatable electrode includes a sealing surface and a cutting edge. One or more non-conductive stop members may be disposed on the first and/or second jaw members that are dimensioned to control the distance between the jaw members when tissue is held therebetween. A rotating assembly is included that is configured to rotate the electrode of the second jaw member from a first operable position wherein the sealing surface of the electrode is generally parallel to the conductive surface of the first jaw member for sealing tissue to a second operable position wherein the cutting edge of the electrode is generally perpendicular to the conductive surface of the first jaw member for dividing tissue.

According to a further aspect of the present disclosure, a method for sealing and dividing tissue is provided. The method includes the initial step of providing an electrosurgical instrument having a housing and a shaft attached thereto that defines a longitudinal axis therethrough. The electrosurgical instrument also includes first and second opposing jaw members coupled to the shaft, the first jaw member having a conductive surface and movable relative to the second jaw member. The second jaw member is fixed relative to the shaft and includes an electrode rotatable about the longitudinal axis. The rotatable electrode includes a first surface for sealing tissue and a second surface for cutting tissue;

The method also includes the steps of: positioning the first surface of the rotatable electrode in generally parallel relation to the conductive surface of the first jaw member; approximating tissue by closing the first and second jaw members and creating a gap distance between the first surface of the second jaw member and the conductive surface of the first jaw member; applying electrosurgical energy to the first surface of the second jaw member and the conductive surface of the first jaw member to effect a tissue seal; opening the first and second jaw members and repositioning the electrode so the second surface of the rotatable electrode is generally perpendicular to the conductive surface of the first jaw member; and closing the first and second jaw members on the tissue seal to divide the tissue along the seal.

BRIEF DESCRIPTION OF THE DRAWINGS

Various embodiments of the subject instrument are described herein with reference to the drawings wherein.

DETAILED DESCRIPTION

Figure 6A:
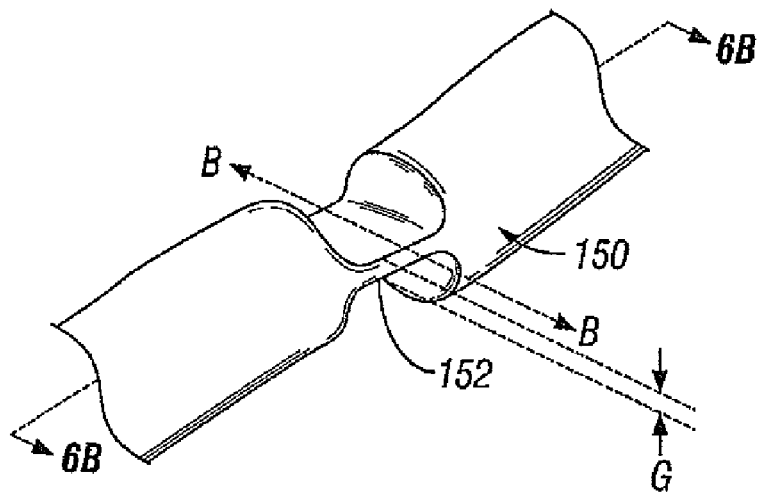
FIG. 6A is an enlarged perspective view of a sealing site of a tubular vessel.

Turning now to the several Figures, one embodiment of an endoscopic bipolar forceps 10 is shown for use with various surgical procedures and generally includes a housing 20, a handle assembly 30, a rotating assembly 80 and an end effector assembly 100 which mutually cooperate to grasp, seal and divide tubular vessels and vascular tissue 150 (FIG. 6A). Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. In the drawings and in the descriptions which follow, the term "proximal", as is traditional, will refer to the end of the forceps 10 which is closer to the user, while the term "distal" will refer to the end which is further from the user. Further, the shaft 12 defines a longitudinal axis "A-A" through the forceps 10.

Figure 1:
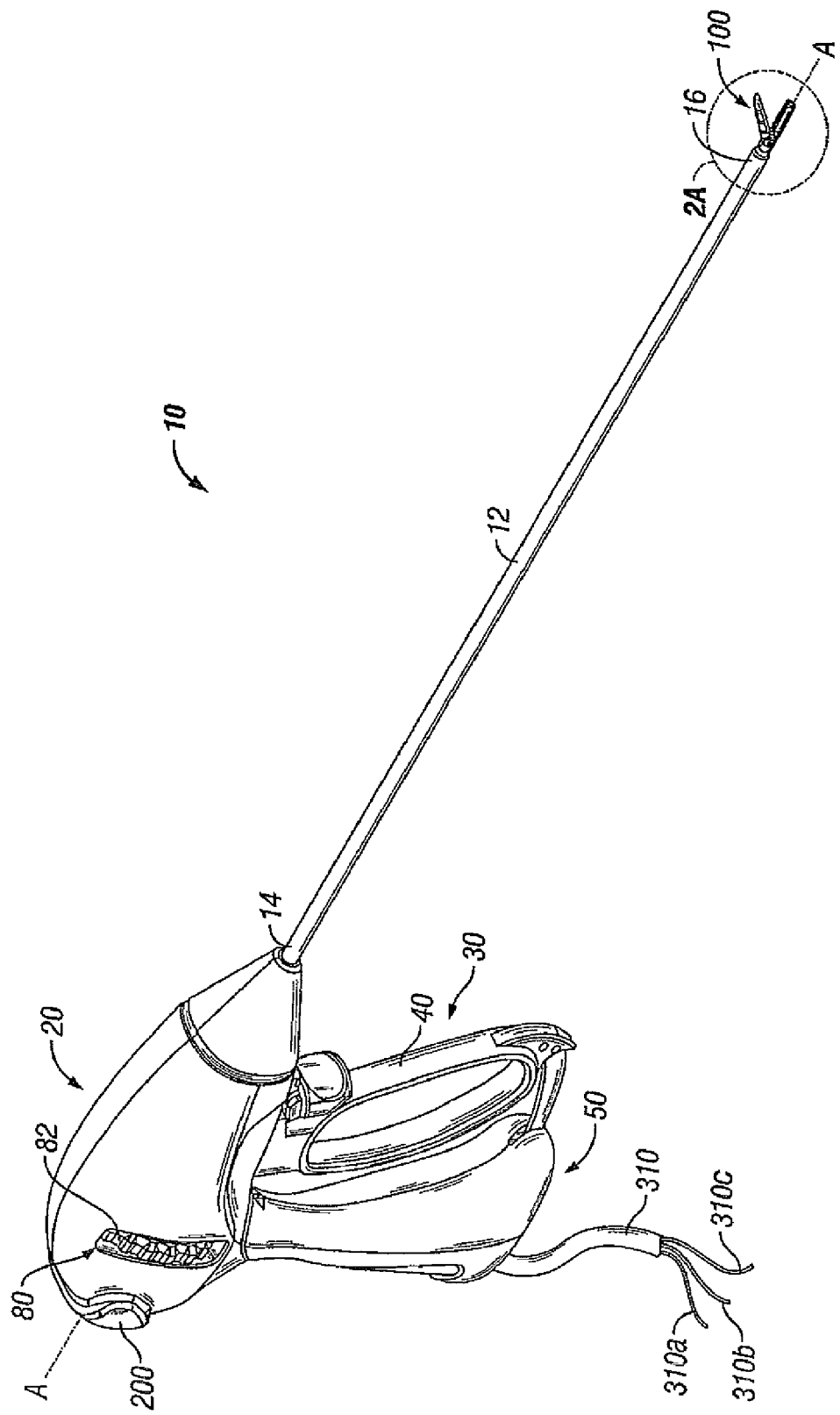
FIG. 1 is a perspective view of an endoscopic forceps showing a handle and an end effector according to the present disclosure.

As best seen in FIG. 1, forceps 10 also includes an electrosurgical cable 310 which connects the forceps 10 to a source of electrosurgical energy, e.g., a generator (not shown). Generators such as those sold by Valleylab—a division of Tyco Healthcare LP, located in Boulder, Colo. are used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL", the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS", the entire contents of which is also incorporated by reference herein.

The generator includes various safety and performance features including isolated output, independent activation of accessories. The electrosurgical generator includes Valleylab's Instant Response™ technology features which provides an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;
Reduced thermal spread and risk of collateral tissue damage;
Less need to "turn up the generator"; and
Designed for the minimally invasive environment.

Cable 310 is internally divided into a plurality of cable leads 310a, 310b, 310c which each transmit electrosurgical energy through their respective feed paths through the forceps 10 to the end effector assembly 100 as explained in more detail below.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 may be integrally associated with the housing 20 and is rotatable approximately 180 degrees in either direction about the longitudinal axis "A-A". Details of the rotating assembly 80 are described in more detail with respect to FIGS. 2A, 2B, 3A, 3B and 5.

Figure 2A:
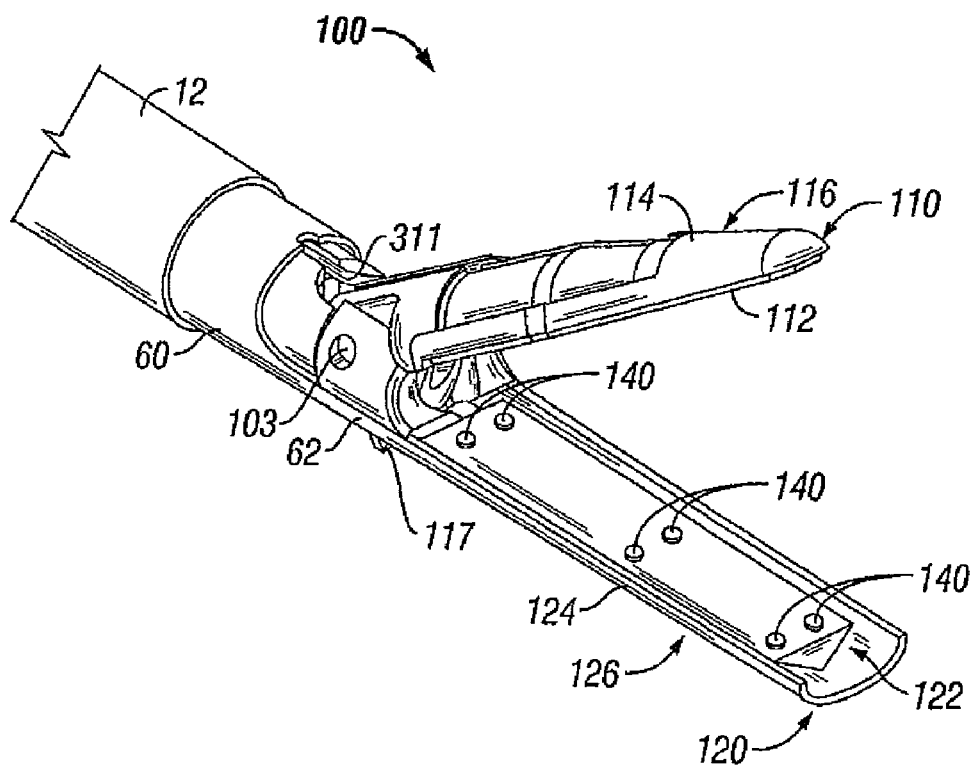
FIG. 2A is an enlarged, left perspective view of the end effector assembly with jaw members shown in an open configuration for sealing vessels.
Figure 2B:
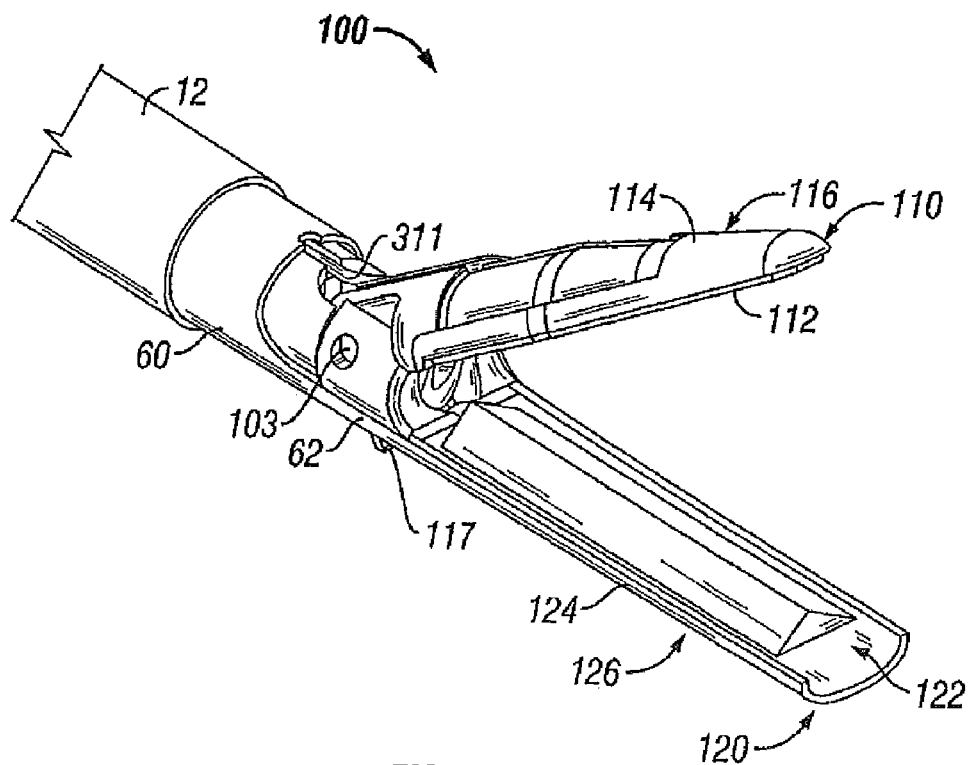
FIG. 2B is an enlarged, left perspective view of the end effector assembly with the jaw members shown in an open configuration for cutting vessels.

As mentioned above, end effector assembly 100 is attached at the distal end 16 of shaft 12 and includes a pair of opposing jaw members 110 and 120 as shown in FIGS. 2A and 2B. Movable handle 40 of handle assembly 30 is ultimately connected to a drive assembly (not shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue 150 (FIG. 6B) therebetween or to cut tissue (FIG. 6C). The specific functions and operative relationships of these elements and the various internal-working components of forceps 10 are described in more detail in commonly assigned, co-pending application U.S. Ser. No. 10/460,926, entitled "VESSEL SEALER AND DIVIDER FOR USE WITH SMALL TROCARS AND CANNULAS" by Dycus et al. which is hereby incorporated by reference herein in its entirety.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

As shown best in FIGS. 2A and 2B, the end effector assembly 100 includes opposing jaw members 110 and 120 which cooperate to effectively grasp tissue 150 for sealing purposes and to divide the tissue 150 once sealed. The end effector assembly 100 is designed as a unilateral assembly, i.e., jaw member 120 is fixed relative to the shaft 12 and jaw member 110 pivots about a pivot pin 103 to grasp tissue 150.

Figure 4:
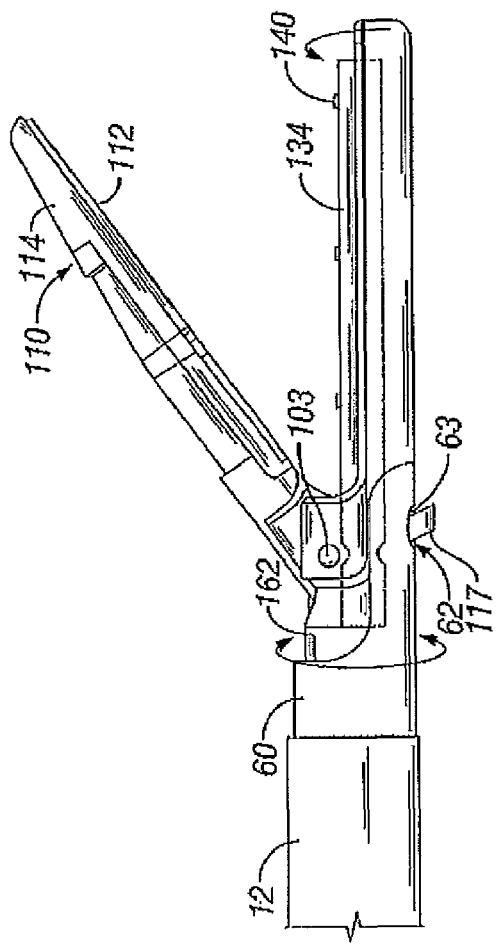
FIG. 4 is an enlarged, side view of the end effector assembly.

More particularly, the unilateral end effector assembly 100 includes one stationary or fixed jaw member 120 mounted in fixed relation to the shaft 12 and pivoting jaw member 110 mounted about a pivot pin 103 attached to the stationary jaw member 120. A reciprocating sleeve 60 is slidingly disposed within the shaft 12 and is remotely operable by the drive assembly (not shown). The above mentioned U.S. patent application Ser. No. 10/460,926 describes one example of a drive assembly which may be utilized for this purpose. The pivoting jaw member 110 includes a detent or protrusion 117 which extends from jaw member 110 through an aperture 62 disposed within the reciprocating sleeve 60. The pivoting jaw member 110 is actuated by sliding the sleeve 60 axially within the shaft 12 such that a distal end 63 of the aperture 62 abuts against the detent 117 on the pivoting jaw member 110 (see FIG. 4). Pulling the sleeve 60 proximally closes the jaw members 110 and 120 about tissue 150 grasped therebetween and pushing the sleeve 60 distally opens the jaw members 110 and 120 for grasping purposes.

As best shown in FIG. 2A, jaw member 110 also includes a jaw housing 116 which has an insulative substrate or insulator 114 and an electrically conducive surface 112. Insulator 114 is preferably dimensioned to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 may be dimensioned to limit and/or reduce many of the known undesirable effects related to tissue sealing, e.g., flashover, thermal spread and stray current dissipation. Alternatively, it is also envisioned that the jaw member 110 may be manufactured from a ceramic-like material and the electrically conductive surface 112 is coated onto the ceramic-like jaw members 110.

It is envisioned that the electrically conductive sealing surface 112 may also include an outer peripheral edge which has a pre-defined radius and the insulator 114 meets the electrically conductive sealing surface 112 along an adjoining edge of the sealing surface 112 in a generally tangential position. Preferably, at the interface, the electrically conductive surface 112 is raised relative to the insulator 114. These and other envisioned embodiments are discussed in co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al., the contents of both are hereby incorporated by reference herein in their entirety.

Figure 3A:
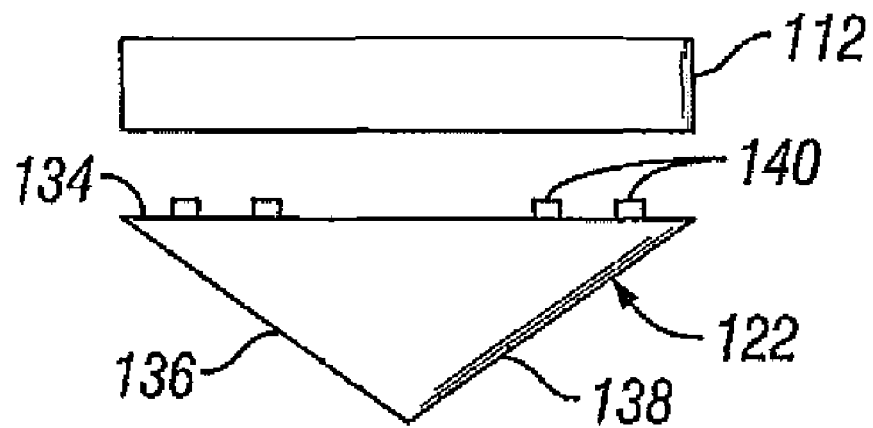
FIG. 3A is an end view of the end effector assembly of FIG. 2A showing the conducting surfaces in a configuration for sealing vessels.
Figure 3B:
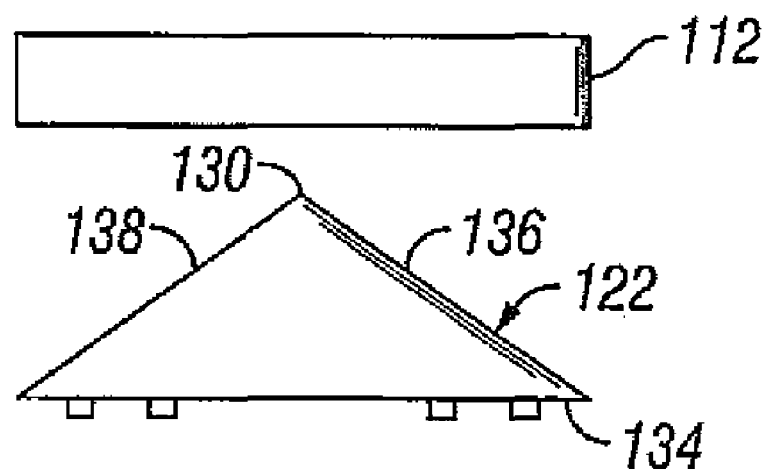
FIG. 3B is an end view of the end effector assembly of FIG. 2B showing the conducting surfaces in a configuration for cutting vessels.

Jaw member 120 includes similar elements to jaw member 110 such as jaw housing 126 having an insulator 124. Unlike jaw member 110, jaw member 120 includes a rotatable electrode 122. The rotatable electrode 122 has at least two operable positions. A first position is employed during vessel sealing and a second position is employed during vessel dividing or cutting. As best seen in FIGS. 3A and 3B, the rotating electrode 122 includes three surfaces, namely, a first surface 134, a second surface 136 and a third surface 138.

Referring to FIG. 3A, when in a first operable position, the first surface 134 of electrode 122 is generally and substantially parallel to the conductive sealing surface 112 of first jaw member 110. In this position, first surface 134 and conductive sealing surface 112 will facilitate grasping of tissue. Upon activation of electrosurgical energy and upon application of pressure within the predefined range of about 3 kg/cm$^2$ to about 16 kg/cm$^2$ and upon grasping the tissue within a predefined gap range of about 0.001 inches to about 0.006 inches, and preferably from about 0.002 inches to about 0.004 inches, the tissue dispersed between the jaw members will seal into a single fused mass with limited demarcation between tissue layers. As explained in more detail below, a series of stop members are operatively associated with at least one of the jaw members to maintain a gap distance "G" (FIG. 6A) between opposing tissue containing surfaces 112 and 134. As explained in the above-identified U.S. patent application Ser. No. 10/460,926, handle 40 and fixed handle 50 include a camming mechanism which, upon activation thereof, maintains pressure between opposing sealing surfaces between about 3 kg/cm$^2$ to about 16 kg/cm$^2$. U.S. patent application Ser. No. 11/044,805, and U.S. patent application Ser. No. 10/427,832 include exemplitive details regarding the various electrical parameters which need to be closely monitored and controlled to optimize the vessel sealing process for various tissue thicknesses and tissue types, the contents of both of which are hereby incorporated by reference herein.

Referring to FIG. 3B, second surface 136 and third surface 138 of electrode 122 meet to form cutting edge 130. When the forceps is selectively rotated to the second operable position, the cutting edge 130 is generally perpendicular to sealing surface 112. When the jaw members 110, 120 are moved to a closed position, cutting edge 130 comes into close proximity with sealing surface 112 to electromechanically sever or cut sealed tissue as will be described below in relation to FIG. 6C.

As mentioned above, rotatable electrode 122 (and/or jaw member 110 of sealing surface 112) includes at least one and preferably a plurality of stop members 140 operatively associated with the first surface 134 of the electrode 122. Stop members 140 are configured to define a gap "G" (FIG. 6A) between opposing sealing surfaces 112 and 134 of jaw members 110 and 120 during tissue sealing. It is envisioned that a series of stop members 140 may be employed on one or both jaw members 110 and 120 (and/or sealing surfaces 112 and 134) depending upon a particular purpose or to achieve a desired result. A detailed discussion of these and other envisioned stop members 140 as well as various manufacturing and assembling processes for attaching and/or affixing the stop members 140 to the jaw members 110, 120 are described in commonly-assigned, co-pending Application Serial No. PCT/US01/11413 entitled "VESSEL SEALER AND DIVIDER WITH NON-CONDUCTIVE STOP MEMBERS" by Dycus et al. which is hereby incorporated by reference in its entirety herein.

Stop members 140 are affixed/attached to the jaw member(s) by stamping, thermal spraying, overmolding and/or by an adhesive. The stop members project from about 0.001 inches to about 0.006 inches and, preferably, from about 0.002 inches to about 0.004 inches from the inner-facing surface of at least one of the jaw members. It is envisioned that the stop members may be made from an insulative material such as parylene, nylon and/or ceramic. Other materials are also contemplated, e.g., syndiotactic polystryrenes such as QUESTRA® manufactured by DOW Chemical, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Figure 5:
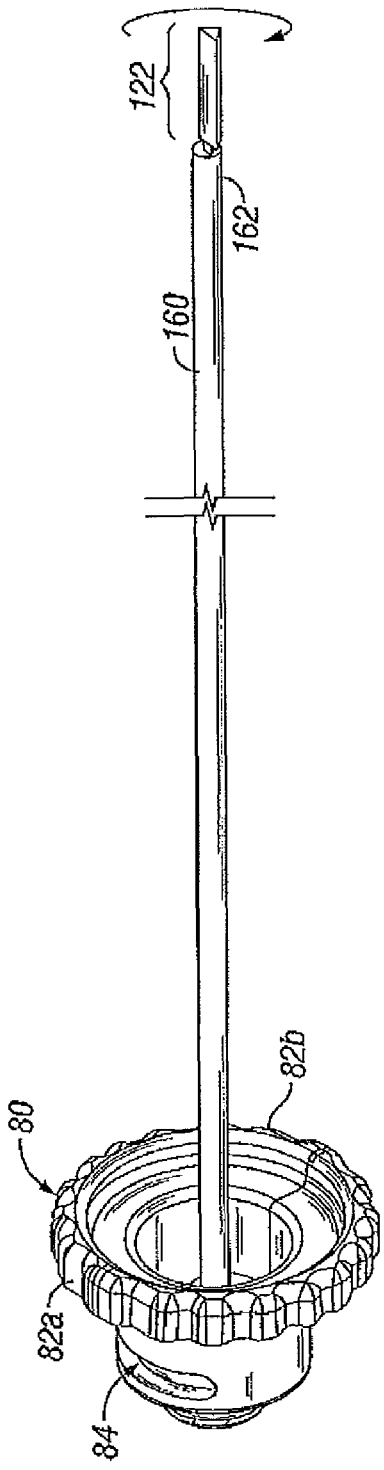
FIG. 5 is an enlarged perspective view of the rotating assembly.

As explained in detail below and as best seen in FIG. 5, rotatable electrode 122 is designed to be fixed to the end of a rotating tube 162 which is part of the rotating assembly 80 such that rotation of the tube 162 via dial 82 will impart rotation to the electrode 122. In contrast to U.S. patent application Ser. No. 10/460,926, the rotating assembly is designed to rotate electrode 122 and not the end effector assembly 100. More particularly, rotating tube 162 includes an elongated guide slot 160 disposed in an upper portion thereof which is dimensioned to carry lead 310a therealong. Lead 310a carries a first electrical potential to movable jaw 110. As explained in more detail below with respect to the internal electrical connections of the forceps, a second electrical connection from lead 310c is conducted through the tube 160 to the electrode 134 of fixed jaw member 120.

The electrical leads 310a, 310b, 310c and 311 are fed through the housing 20 by electrosurgical cable 310. More particularly, the electrosurgical cable 310 is fed into the bottom of the housing 20 through fixed handle 50. Lead 310c extends directly from cable 310 into the rotating assembly 80 and connects to electrode 122 to conduct the second electrical potential to fixed jaw member 120. Leads 310a and 310b extend from cable 310 and connect to the hand switch or joy-stick-like toggle switch 200. The specific functions and operative relationships of these elements and the various internal-working components of forceps 10 are described in more detail in commonly assigned, co-pending application U.S. Ser. No. 10/460,926, entitled "VESSEL SEALER AND DIVIDER FOR USE WITH SMALL TROCARS AND CANNULAS" by Dycus et al. which is hereby incorporated by reference herein in its entirety.

When the switch 200 is depressed, electrosurgical energy is transferred through leads 310a and 310c to jaw members 110 and 120, respectively. It is envisioned that a safety switch or circuit (not shown) may be employed such that the switch cannot fire unless the jaw members 110 and 120 are closed and/or unless the jaw members 110 and 120 have tissue 150 held therebetween. In the latter instance, a sensor (not shown) may be employed to determine if tissue 150 is held therebetween. In addition, other sensor mechanisms may be employed which determine pre-surgical, concurrent surgical (i.e., during surgery) and/or post surgical conditions. Still other sensor mechanisms, e.g., a toggle switch or the like, may be positioned on the tube 162 to determine the relative position of electrode 122, i.e., seal activation or cut activation.

The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003, the entire contents of which are hereby incorporated by reference herein.

It is envisioned that cable leads 310a and 310c are fed through respective halves 82a and 82b of the rotating assembly 80 in such a manner to allow rotation of the shaft 162 (via rotation of the rotating assembly 80) in the clockwise or counter-clockwise direction without unduly tangling or twisting the cable leads 310a and 310c. More particularly, each cable lead 310a and 310c is fed through a series of conjoining slots, e.g., 84, located in the two halves 82a and 82b of the rotating assembly 80. Each conjoining pair of slots are large enough to permit rotation of the rotating assembly 80 without unduly straining or tangling the cable leads 310a and 310c. The presently disclosed cable lead feed path is envisioned to allow rotation of the rotation assembly approximately 180 degrees in either direction, which, in turn, rotates electrode 122 from a first position for sealing tissue to a second position for cutting tissue.

Figure 6B:
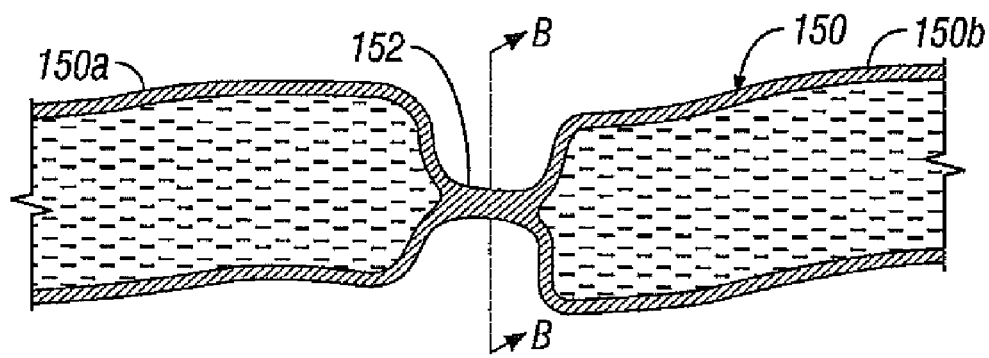
FIG. 6B is a longitudinal cross-section of the sealing site taken along line 6B-6B of FIG. 6A.
Figure 6C:
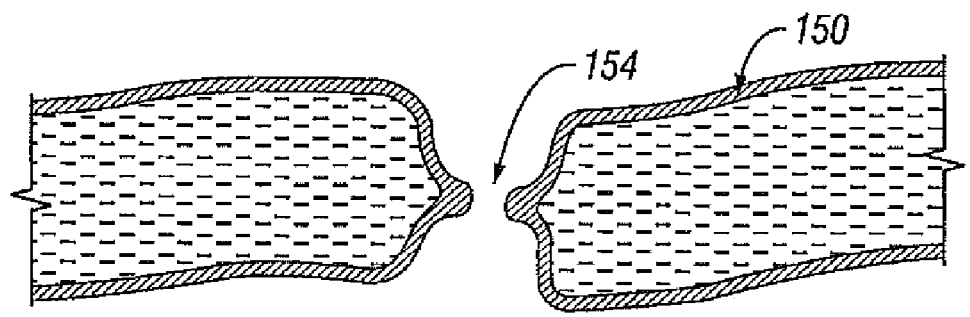
FIG. 6C is a longitudinal cross-section of the sealing site of FIG. 6A after separation of the tubular vessel.

FIGS. 6A through 6C illustrate the sealing and cutting of tissue employing the forceps 10 according to the present disclosure. Before approximating tissue, a user will select an operable position of rotatable electrode 122 via rotating assembly 80. Here, the electrode 122 is placed in the first operable position to perform vessel sealing where the first surface 134 is generally parallel to sealing surface 112 (see FIG. 3A). As the handle 40 is squeezed, the reciprocating sleeve 60 is pulled proximally which, in turn, causes aperture 62 of sleeve 60 to proximally cam detent 117 and close the jaw member 110 relative to jaw member 120. The reciprocating sleeve's 60 load is converted to a torque about the jaw pivot 103. As a result, a specific closure force can be transmitted to the opposing jaw members 110 and 120 between about 3 kg/cm$^2$ to about 16 kg/cm$^2$.

As can be appreciated and as discussed in U.S. patent application Ser. No. 10/460,926, the unique combination of the mechanical advantage of the over-the-center pivot along with the compressive force associated with the drive assembly facilitate and assure consistent, uniform and accurate closure pressure about the tissue 150 within the desired working pressure range of about 3 kg/cm$^2$ to about 16 kg/cm$^2$ and, preferably, about 7 kg/cm$^2$ to about 13 kg/cm$^2$. By controlling the intensity, frequency and duration of the electrosurgical energy applied to the tissue 150, the user can seal the tissue. As mentioned above, two mechanical factors play an important role in determining the resulting thickness of the sealed tissue and effectiveness of the seal 150, i.e., the pressure applied between opposing jaw members 110 and 120 and the gap distance "G" between the opposing sealing surfaces 112, 134 of the jaw members 110 and 120 during the sealing process. However, thickness of the resulting tissue seal 152 cannot be adequately controlled by force alone. In other words, too much force and the two jaw members 110 and 120 would touch and possibly short resulting in little energy traveling through the tissue 150 thus resulting in a bad tissue seal 152. Too little force and the seal 152 would be too thick.

Applying the correct force is also important for other reasons: to oppose the walls of the vessel; to reduce the tissue impedance to a low enough value that allows enough current through the tissue 150; and to overcome the forces of expansion during tissue heating in addition to contributing towards creating the required end tissue thickness which is an indication of a good seal 150.

As mentioned above, at least one jaw member, e.g., 120, may include a stop member 140 operatively associated therewith which limits the movement of the two opposing jaw members 110 and 120 relative to one another. For example, the stop member 140 may extend from the sealing surface 134 a predetermined distance according to the specific material properties (e.g., compressive strength, thermal expansion, etc.) to yield a consistent and accurate gap distance "G" during sealing (FIG. 6A). The gap distance between opposing sealing surfaces 112 and 134 during sealing ranges from about 0.001 inches to about 0.006 inches and, more preferably, between about 0.002 and about 0.004 inches.

Alternatively, the non-conductive stop members 140 can be molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic or porcelain material onto the surface of the jaw member 110 and 120 to form the stop members 140. Several thermal spraying techniques are contemplated which involve depositing a broad range of heat resistant and insulative materials on various surfaces to create stop members 140 for controlling the gap distance between electrically conductive surfaces 112 and 134.

As energy is being selectively transferred to the end effector assembly 100, across the jaw members 110 and 120 and through the tissue 150, a tissue seal 152 forms isolating two tissue halves 150*a* and 150*b*. At this point and with other known vessel sealing instruments, the user must remove and replace the forceps 10 with a cutting instrument (not shown) to divide the tissue halves 150*a* and 150*b* along an approximate center line B-B of the tissue seal 152. As can be appreciated, this is both time consuming and tedious and may result in inaccurate tissue division across the tissue seal 152 due to misalignment or misplacement of the cutting instrument along the ideal tissue cutting plane, e.g., center line B-B.

Once the tissue seal 152 forms, the jaw members 110 and 120 may be opened by re-grasping the handle 40. Once the jaw members are opened, the rotatable electrode 122 is moved into its second operable position via rotating assembly 80, where cutting edge 130 is generally perpendicular to sealing surface 112. Once the electrode 122 is set, the handle 40 is re-grasped closing jaw members 110 and 120 bringing cutting edge 130 into close proximity of sealing surface 112 to divide tissue 150 along at point 154. The tissue may be cut utilizing mechanical cutting action, electro-mechanical cutting action or simply electrical cutting action depending upon a particular purpose and depending upon the particular configuration of cutting edge 130.

It can be appreciated since forceps 10 can seal and divide tissue without removing the forceps 10 from the operative site the intended procedure can be performed more quickly. Additionally, the seal 152 will be divided uniformly since the user will not have to locate the center of the seal after inserting a different instrument, e.g., a cutting instrument.

From the foregoing and with reference to the various figure drawings, those skilled in the art will appreciate that certain modifications can also be made to the present disclosure without departing from the scope of the same. For example, the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120 and subsequently select the appropriate energy to selectively cut the tissue. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003, the entire contents of which are hereby incorporated by reference herein.

It is envisioned that the outer surface of the end effector assembly 100 may include a nickel-based material, coating, stamping, metal injection molding which is designed to reduce adhesion between the jaw members 110 and 120 with the surrounding tissue during activation and sealing. Moreover, it is also contemplated that the conductive surfaces 112 and 134 of the jaw members 110 and 120 may be manufactured from one (or a combination of one or more) of the following materials: nickel-chrome, chromium nitride, Med-Coat 2000 manufactured by The Electrolizing Corporation of OHIO, inconel 600 and tin-nickel. The tissue conductive surfaces 112 and 134 may also be coated with one or more of the above materials to achieve the same result, i.e., a "non-stick surface". As can be appreciated, reducing the amount that the tissue "sticks" during sealing/and cutting improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 134 made from or coated with Ni200, Ni201 (~100% Ni) also showed improved non-stick performance over typical bipolar stainless steel electrodes.

As can be appreciated, locating the switch 200 on the forceps 10 has many advantages. For example, the switch 200 reduces the amount of electrical cable in the operating room and eliminates the possibility of activating the wrong instrument during a surgical procedure due to "line-of-sight" activation. It is also envisioned that the switch 200 may be disposed on another part of the forceps 10, e.g., the fixed handle 50, rotating assembly 80, housing 20, etc.

It is also envisioned that the forceps may be dimensioned to include a fixed gap within the range of about 0.001 inches to about 0.006 inches by providing a stop member on another part of the end effector assembly, e.g., proximal and/or distal to the conductive surfaces, on the insulative housing 116 and/or 126, and/or as part of the pivot 103. In addition, it is envisioned that the detent 117 and aperture 62 arrangement may be dimensioned to limit the distance between conductive surfaces 112 and 122.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A method for sealing and dividing tissue, the method comprising the steps of:
    providing an electrosurgical instrument comprising:
        a housing having a shaft attached thereto, the shaft defining a longitudinal axis therethrough; and
        first and second opposing jaw members coupled to the shaft, the first jaw member having a conductive surface and movable relative to the second jaw member, the second jaw member fixed relative to the shaft and having a rotatable electrode positioned therein, the rotatable electrode rotatable about the longitudinal axis and including a first surface for sealing tissue and a second surface for cutting tissue;

positioning the first surface of the rotatable electrode in generally parallel relation to the conductive surface of the first jaw member;

clamping down on tissue by closing the first and second jaw members and creating a gap distance between the first surface of the second jaw member and the conductive surface of the first jaw member;

applying electrosurgical energy to the first surface of the second jaw member and the conductive surface of the first jaw member to effect a tissue seal;

opening the first and second jaw members and repositioning the rotatable electrode so the second surface of the rotatable electrode is generally perpendicular to the conductive surface of the first jaw member; and closing the first and second jaw members on the tissue seal to divide the tissue along the seal.

2. A method according to claim 1, wherein the providing step includes providing at least one non-conductive stop member operatively associated with at least one of the first and second jaw members to control the gap distance between the jaw members when tissue is held therebetween;

3. A method according to claim 1, wherein the closing step further includes the step of applying electrosurgical energy to the second surface of the second jaw member and the conductive surface of the first jaw member to effect tissue cutting.

4. A method according to claim 1, wherein the rotatable electrode further includes a third surface, wherein the second and third surfaces meet at an apex to form a cutting edge to facilitate cutting tissue.

5. A method according to claim 2, wherein the at least one non-conductive stop member is on the first surface of the rotatable electrode.

6. A method according to claim 1, wherein the rotatable electrode is operably coupled to an end of a rotating tube that is part of a rotating assembly operably associated with the electrosurgical instrument such that rotation of an actuator imparts the rotation to the rotatable electrode about the longitudinal axis.

7. A method according to claim 6, wherein the rotating tube includes an elongated guide slot disposed in an upper portion thereof dimensioned to carry a first lead therealong, the first lead carrying a first electrical potential to the first jaw member.

8. A method according to claim 7, wherein a second electrical potential from a second lead is conducted through the rotating tube to the rotatable electrode of the second jaw member.

9. A method according to claim 1, wherein the step of clamping further includes the step transmitting a specific closure force to the first jaw member against the second jaw member, wherein the specific closure force is between the range from about 3 kg/cm$^2$ to about 16 kg/cm$^2$.

* * * * *